United States Patent [19]

Hartmann

[11] 4,280,965

[45] Jul. 28, 1981

[54] PREPARATION OF CYANO SUBSTITUTED BENZYL ESTERS

[75] Inventor: Ludwig A. Hartmann, Wilmington, Del.

[73] Assignee: ICI Americas Inc., Wilmington, Del.

[21] Appl. No.: 142,360

[22] Filed: Apr. 21, 1980

[51] Int. Cl.³ .................. C07C 120/00; C07C 121/66
[52] U.S. Cl. ............................................... 260/465 D
[58] Field of Search .................................. 260/465 D

[56] References Cited

U.S. PATENT DOCUMENTS

| | | | |
|---|---|---|---|
| 3,835,176 | 9/1974 | Matsuo et al. | 260/465 D |
| 4,110,362 | 8/1978 | Sheldon et al. | 260/465 D |

*Primary Examiner*—Dolph H. Torrence

[57] ABSTRACT

An improved process for preparing cyano substituted benzyl esters is disclosed. The process involves reacting an acid halide with an aldehyde and a water soluble cyanide in water in the presence of a tetraalkyl ammonium halide wherein each alkyl group contains from 1 to about 4 carbon atoms. The resulting benzyl esters are particularly useful as insecticides.

7 Claims, No Drawings

PREPARATION OF CYANO SUBSTITUTED BENZYL ESTERS

BACKGROUND OF THE INVENTION

1. Field of the Invention

The present invention relates generally to an improved process for preparing certain benzyl ester insecticides. More particularly, the invention relates to a process in which an acid halide is reacted with an aldehyde and a water soluble cyanide in water and in the presence of a tetraalkyl ammonium halide wherein each alkyl group contains from 1 to about 4 carbon atoms.

2. Description of the Prior Art

Benzyl esters of the pyrethroid type having insecticidal activity have been described in the literature. See, in this regard, U.S. Pat. No. 4,024,163 issued to Elliott et. al. This patent discloses a number of synthetic esters which may be represented by the following general formula:

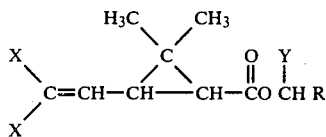

wherein R represents a substituted or unsubstituted aromatic group, Y represents hydrogen or cyano, and X represents halogen.

One particularly interesting group of these materials are those in which Y in the above formula represents a cyano group. However, one problem in the processes previously available for the preparation of these cyano substituted materials is the requirement that the esterification reaction be carried out in the presence of relatively large amounts of organic solvents. As is well known, the use of such solvents introduces a number of problems into the commercialization of the process. In addition, the previously available processes often involved one or more of the following: low yields, long reaction times and low purity.

One method for preparing cyano substituted benzyl esters of the general type indicated above is disclosed in U.S. Pat. No. 3,835,176 issued to Matsuo et. al. This patent relates to alpha-cyanobenzyl cyclopropanecarboxylates and discloses that these materials may be prepared by reacting an acid halide and an aldehyde in an aqueous solution of sodium or potassium cyanide and an aprotic solvent. Specifically, this patent indicates that "a mixture of the acid chloride . . . and the aldehyde . . . or a solution of the mixture in an aprotic solvent is added to an aqueous solution of sodium or potassium cyanide, and the resulting mixture is stirred to obtain the alpha-cyanobenzyl-cyclopropanecarboxylate" (column 3, lines 49-55).

Another reference, U.S. Pat. No. 4,110,361 issued to Sheldon et. al., discloses basically the same process and adds the use of an onium catalyst to the reaction mixture. In accordance with the teachings of this patent, either a quarternary onium compound or a sulfonium compound may be employed as a catalyst in this reaction. A number of suitable onium compounds are disclosed in the reference. However, as noted above, the process requires a relatively large amount of an aprotic solvent.

SUMMARY OF THE INVENTION

In accordance with the present invention it has been found that cyano substituted benzyl esters can be prepared in an aqueous medium if there is included in the reaction mixture a catalytic amount of tetraalkyl ammonium halide wherein each alkyl group contains from 1 to about 4 carbon atoms.

DESCRIPTION OF THE PREFERRED EMBODIMENTS

As mentioned above, the process of the present invention involves reacting an acid halide, an aldehyde, and a water soluble cyanide in an aqueous medium and in the presence of a tetraalkyl ammonium halide. Each of these components is described separately below.

Aldehyde

The aldehydes useful in the process of the present invention may be represented by the following general formula:

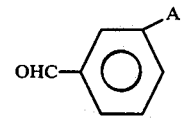

wherein A represents a phenoxy (—OC$_6$H$_5$), phenylthio (—SC$_6$H$_5$) or benzyl (—CH$_2$C$_6$H$_5$) group. Representative aldehydes which may be employed include 3-phenoxybenzaldehyde, 3-phenylthio-benzaldehyde and 3-benzylbenzaldehyde. A preferred aldehyde for use in the process is one in which A in the above formula represents a phenoxy group-i.e., 3-phenoxybenzaldehyde.

Acid Halide

The acid halide employed in the process of the present invention may be represented by the following general formula:

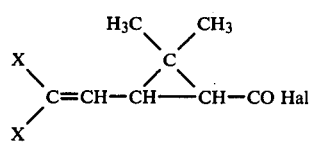

wherein each X independently represents CF$_3$ or halogen, preferably chlorine or bromine and Hal represents halogen, preferably chlorine. Representative acid halides which may be utilized include 3-(2,2-dichlorovinyl)-2,2-dimethylcyclopropane-1-carboxylic acid chloride; 3-(2,2-dibromovinyl)-2,2-dimethyl-cyclopropane-1-carboxylic acid chloride and 3-(2-bromo-2-trifluoromethylvinyl)-2,2-dimethyl-cyclopropane-1-carboxylic acid chloride. The amount of acid halide should be at least equal, on a molar basis, to the amount of aldehyde used in the reaction. It is preferred to employ an excess of acid halide, generally up to about a 10 mole percent excess based on the amount of aldehyde used. Especially preferred results have been achieved with an excess of acid halide equal to from about 2 to about 5 mole percent based on the amount of aldehyde.

Water Soluble Cyanide

Any cyanide which is soluble in water may be utilized in the process of the present invention. Preferred results are achieved with the alkali or alkaline earth metal cyanides, preferably the alkali metal cyanides such as sodium cyanide and potassium cyanide. Because of its availability, and good solubility in water, especially preferred results are achieved with sodium cyanide.

The amount of cyanide used in the process should be equal to at least one mol per mol of aldehyde. Preferred results are achieved with an excess of cyanide in an amount equal to up to about a 30 mol percent excess based on the amount of aldehyde used in the reaction. Especially preferred results are achieved with about a 20 mol percent excess of cyanide over the aldehyde.

Tetraalkyl Ammonium Halide

In accordance with the present invention, it has been found to be critical to carry out the acid halide/aldehyde/cyanide reaction in the presence of a tetraalkyl ammonium halide in which each alkyl group contains from 1 to about 4 carbon atoms. At least 3, and preferably all 4, of the alkyl substituents are the same in any one compound. Although other halide substituents may be used, it is preferred to employ these materials as the bromide because of the availability and relatively low cost of these materials. Especially preferred results have been achieved when tetraethyl ammonium bromide (TEAB) is used as the alkyl ammonium halide. With these materials, it has been found that the reaction can be carried out in a reaction medium consisting essentially of water. Also, the reaction results in a high yield of the desired product of high purity.

Although any amount of ammonium halide which is effective to catalyze the reaction may be used, preferred results have been achieved with an amount of this material equal to from about 3% to about 6% by weight based upon the weight of aldehyde used in the reaction. Although the reaction can be carried out with greater amounts of tetraalkyl ammonium halide, no advantages have been seen when this is done. Especially preferred results are achieved with an amount of tetraethyl ammonium halide equal to about 5% by weight based upon the weight of aldehyde in the reaction.

The process of the present invention may be carried out in any one of a number of ways. Preferred results are achieved by first preparing a mixture of the acid halide and aldehyde and adding this mixture to an aqueous solution of the water soluble cyanide and tetraethyl ammonium bromide. The aldehyde may be either a solid or a liquid. If it is a solid it is preferably melted before being combined with the acid halide. The mixture of acid halide and aldehyde can conveniently be prepared by adding the aldehyde to the liquid acid halide at a temperature less than about 10° C. The mixture is preferably kept cool to eliminate or reduce any premature reaction between the components. Alternatively, the acid halide and aldehyde can be added simultaneously from separate sources but this method is less preferred. The resulting acid halide-aldehyde mixture is then added to the water soluble cyanide-tetraethyl ammonium bromide aqueous solution over a period of time. The addition is carried out as rapidly as possible at a rate such that the reaction temperature does not rise above about 40° C. External cooling is then applied and the temperature of the reaction mixture maintained at from about 25° C. to about 40° C. during the reaction. Preferred results are achieved when the temperature is maintained at from about 30° C. to about 35° C. during the course of the reaction.

As noted above, one advantage of the use of $C_1$ to $C_4$ tetraalkyl ammonium halides is that the reaction can be conducted in an aqueous medium preferably consisting only of water. In order to make most efficient use of the available reactor volume the minimum amount of water which is sufficient to allow good mixing of the reactants and sufficient to dissolve all of the cyanide used in the reaction should be utilized. Although an all aqueous reaction medium is preferred, some organic solvent may, if desired, be included in the reaction mixture.

The reaction is completed by simply stirring the reaction mixture for a suitable period of time, generally about two hours. After the reaction is completed the benzyl ester product may be separated and any impurities or unreacted starting materials removed in any one of several ways. Another advantage of this process is that it is relatively easy to separate the product from the reaction mixture. In one method of separation an additional quantity of water equal to approximately double the quantity originally used in the reaction mixture is added and the mixture is stirred for a short period of time (5–10 minutes). At the end of this time, stirring is stopped and the cyano substituted benzyl ester which is a viscous liquid allowed to settle out of the reaction mixture. The aqueous phase is discarded and the product washed twice with water by mixing at an elevated temperature of about 60° for short periods of time. This treatment removes traces of cyanide and acid halide. If desired, the washes can be conducted with hot brine which also removes traces of cyanide and acid chloride or with a dilute aqueous caustic (sodium hydroxide) or carbonate solution which hydrolyzes any unreacted acid halide and removes excess unreacted acid.

In another separation method, an aprotic solvent such as those disclosed in the Sheldon et al. patent mentioned above is utilized. The desired product dissolves in the solvent and forms a separate phase from the aqueous reaction mixture. Any aprotic solvent which is immiscible with water may be utilized in this separation technique. Representative solvents include aromatic hydrocarbons and chlorinated hydrocarbons. Examples of these materials include benzene, toluene, o-, m- and p-xylene, trimethylbenzenes, dichloromethane, 1,2-dichloromethane, chloroform, monochlorobenzene and 1,2- and 1,3-dichlorobenzene Tenneco 500 (a mixture of aromatic solvents available from Tenneco Chemicals, Inc.), Aromatics 150 (a mixture of $C_9$ to $C_{12}$ aromatics available from Exxon Company) and Solvesso 150 (a mixture of aromatics also available from Exxon). Particularly preferred results have been achieved with a material identified as Aromasol H which is an aromatic petroleum based solvent consisting of approximately 75% isomeric trimethyl benzenes together with other high-boiling aromatic compounds and which is available from the Petrochemicals Division of Imperial Chemical Industries Ltd. In order to separate the ester product from the reaction mixture, a mixture of the aprotic solvent and an additional amount of water is added to the reaction mixture and stirred at about 40° C. The desired product dissolves in the aprotic solvent which forms a separate layer which can easily be separated. The aprotic solvent is then treated with a small amount (from about 1 to about 5% by volume based on the total volume) of methanol at a temperature of from about 50°

C. to about 60° C. in order to remove any unreacted acid chloride by converting it to the corresponding methyl ester. The solvent layer is then washed with brine and/or caustic or carbonate solution as in the other separation technique described above. The resulting purified solution may be vacuum sparged in order to remove any HCN or HCl present, and the aprotic solvent removed by distillation. Preferably, only part of the aprotic solvent is removed by distillation resulting in a solution containing about 50% by weight of the cyano substituted benzyl ester.

The resulting benzyl esters are useful as pesticides, particularly insecticides as disclosed in the Elliott et al. patent referred to above.

In order to describe the present invention so that it may be more clearly understood, the following examples are set forth. In the examples, the following standard materials were employed:

Acid Halide A refers to 3-(2,2-dichlorovinyl)-2,2-dimethyl-cyclopropane-1-carboxylic acid chloride having the following structural formula

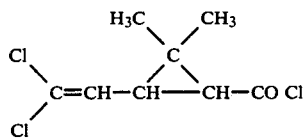

Aldehyde A refers to 3-phenoxybenzaldehyde having the following formula:

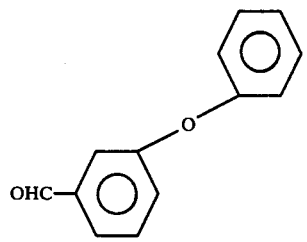

Aromasol H refers to an aromatic, petroleum based solvent available from Imperial Chemical Industries Ltd., Petrochemicals Division and described above.

EXAMPLE 1

33.7 grams of molten 99% pure Aldehyde A was combined with 42.1 grams of 96% pure Acid Halide A (0.178 mol of pure Acid Halide A) at a temperature of from 5° to 8° C. while stirring. The resulting mixture was slowly added to a solution of:

10 grams (0.204 mol) of sodium cyanide, and
1.5 grams (0.007 mol) of tetraethyl ammonium bromide in 33 ml of water.

The temperature of the resulting mixture was allowed to rise to about 30° C. during the first 15 minutes of the addition and was maintained at 30° C. by external cooling during the addition of the remainder of the acid halide-aldehyde mixture. The total addition time was equal to 40 minutes. After the addition was completed, the reaction was continued and the temperature maintained at 30° C. for 2 hours.

At the end of this time 75 ml of water was added and the mixture stirred at 30° to 35° C. for 5 minutes. The product was then allowed to settle to the bottom of the reaction mixture and was separated from the aqueous layer which was discarded. The product was then washed twice by stirring with 80 ml of water at 60° C. for 15 minutes. The product was then vacuum stripped at a pot temperature of between 50° and 80° C. and a vacuum below 1 mm of mercury. The resulting product weighed 70.4 grams and contained 92% by weight of the desired product. The yield of ester product was equal to 90.5% based on the weight of aldehyde used in the reaction.

EXAMPLE 2

84.25 grams of molten 99% pure Aldehyde A (0.423 mol of pure Aldehyde A) was combined with 102 grams of 96% pure Acid Halide A (0.431 mol of pure Acid Halide A) at 7° C. while stirring. 74.7 grams of the resulting mixture was slowly added to a solution of:

10 grams (0.204 mol) of sodium cyanide, and
1.5 grams (0.007 mol) of tetraethyl ammonium bromide in 33 ml of water.

The temperature of the resulting mixture was allowed to rise to about 30° C. during the first 15 minutes of the addition and was maintained at 30° C. by external cooling during the addition of the remainder of the acid halide-aldehyde mixture. The total addition time was 50 minutes. After the addition was completed, the temperature was maintained at from 30° to 31° C. by external cooling for 25 minutes and then by a warm water bath for an additional 1 hour and 35 minutes. The total reaction time was equal to 2 hours.

At the end of this time, a mixture of 85 grams of Aromasol H and 30 ml of water was added and the solution was warmed to 35° C. for 20 minutes. Separation of the mixture into two layers took place within the first 5 minutes. The resulting Aromasol H layer was separated into two equal portions. One portion was washed twice with 40 ml of a brine solution at 60° C. The purified Aromasol H solution was vacuum sparged for 20 minutes at 65° and 200 mm. The solution was then distilled at a bath temperature of between 80° and 89° C. and 18 mm of pressure to remove 18 grams of distillate. The resulting Aromasol solution of the desired ester weighed 57 grams. Analysis of this material indicated that it contained 39.1% Aromasol H, 57.1% by weight of the cyano substituted benzyl ester, and 0.5% by weight of unreacted aldehyde. The yield of ester was equal to 91.9% based on the weight of aldehyde used in the reaction.

What is claimed is:

1. A process for preparing a cyano substituted benzyl ester which comprises reacting an acid halide having the following general formula:

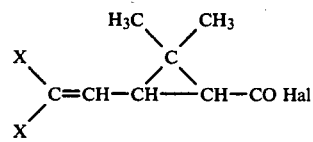

wherein each X independently represents $CF_3$ or halogen and Hal represents halogen, an aldehyde having the following general formula:

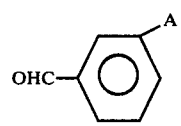

wherein A is selected from the group consisting of phenoxy, phenylthio and benzyl, and a water soluble cyanide in water in the presence of a tetraalkyl ammonium halide wherein each alkyl group contains from 1 to about 4 carbon atoms.

2. A process, as claimed in claim 1, wherein the acid halide is 3-(2,2-dichlorovinyl)-2,2-dimethyl-cyclopropane-1-carboxylic acid chloride.

3. A process, as claimed in claim 1, wherein the aldehyde is 3-phenoxybenzaldehyde.

4. A process, as claimed in claim 1, wherein the water soluble cyanide is sodium cyanide.

5. A process, as claimed in claim 1, wherein the tetraalkyl ammonium halide is tetraethyl ammonium bromide.

6. A process, as claimed in claim 1, wherein the amount of tetraalkyl ammonium halide is equal to an amount at least sufficient to accelerate the rate of the reaction and less than about 6% by weight based upon the weight of aldehyde in the reaction.

7. A process, as claimed in claim 1, wherein the amount of acid halide is equal to at least one mol per mol of aldehyde in the reaction.

* * * * *